United States Patent [19]

Curé

[11] 4,059,996
[45] Nov. 29, 1977

[54] MOLTEN METAL SAMPLE CUP CONTAINING BLOB FOR PROMOTING CARBIDE FORMATION

[75] Inventor: Omer Paul Curé, Diepenbeek, Belgium

[73] Assignee: Electro-Nite Co., Philadelphia, Pa.

[21] Appl. No.: 742,293

[22] Filed: Nov. 16, 1976

[30] Foreign Application Priority Data

Nov. 20, 1975 Belgium .................................. 2/54666

[51] Int. Cl.² .......................... G01N 1/10; G01K 13/12
[52] U.S. Cl. ................................. 73/354; 73/425.4 R; 73/DIG. 9; 249/DIG. 4; 164/4; 164/57; 165/150
[58] Field of Search ............. 249/DIG. 4; 164/4, 150, 164/55, 56, 57, 58, 59; 73/354, 425.4, DIG. 9; 106/38.22, 38.27

[56] References Cited

U.S. PATENT DOCUMENTS

| | | | |
|---|---|---|---|
| 2,250,488 | 7/1941 | Lorig et al. | 106/38.22 X |
| 3,546,921 | 12/1970 | Bourke et al. | 73/DIG. 9 |
| 3,704,621 | 12/1972 | Zickefoose et al. | 73/DIG. 9 X |
| 3,946,594 | 3/1976 | Surinx | 73/DIG. 9 X |
| 4,003,425 | 1/1977 | Middleton | 106/38.27 X |

FOREIGN PATENT DOCUMENTS

| | | | |
|---|---|---|---|
| 2,110,922 | 9/1972 | Germany | 249/DIG. 4 |
| 44-20721 | 9/1969 | Japan | 106/38.3 |
| 320,329 | 1/1972 | U.S.S.R. | 106/38.27 |

*Primary Examiner* — Ronald J. Shore
*Attorney, Agent, or Firm* — Seidel, Gonda & Goldhammer

[57] ABSTRACT

A molten metal sample cup is provided with temperature sensing means to detect phase change in the metal within the cup as a metal sample solidifies. A blob of material which promotes the formation carbides is attached to the inside of the cup to contact the molten metal therein. The blob material comprises a carbide stabilizer selected from the group consisting of bismuth, boron, cerium, lead, magnesium and tellurium, a refractory material and a hydrogen evolving material.

11 Claims, 2 Drawing Figures

MOLTEN METAL SAMPLE CUP CONTAINING BLOB FOR PROMOTING CARBIDE FORMATION

BACKGROUND OF THE INVENTION

The present invention relates to an improved molten metal sample cup for measuring solidifying temperatures of cast iron, steel and similar materials. A molten metal receiving cup, usually made from suitable refractory materials, such as foundry sand and cement, is fitted with a thermocouple for determining temperature, phase changes of the molten metal, thermal arrest temperatures and the like. For example, see the cups of U.S. Pat. No. Re. 26,409.

In present molten metal receiving cups, the thermocouple hot junction may be supported within the cup in any number of ways so as to contact the molten metal when the metal is poured into the cup. The thermocouple is able to sense the temperature of the molten metal as it cools, and a temperature versus time chart is plotted. By interpreting the chart, metallurgists can determine the characteristics of the molten metal.

Usually, the samplers are provided with an inside coating to insulate the thermocouple and/or to influence the solidification of the molten metal. When cast iron cools, it solidifies into a combination of gray and white iron. Gray iron refers to iron having enhanced graphite formation. White iron refers to iron having enhanced carbide formation, and the process of forming white iron is called white solidification.

The molten metal sample cups are frequently coated with a material which promotes the formation of either gray iron or white iron. When white solidification is desired, a material which enhances the formation of carbides is added to the coating on the inside of the sample cup. Typical additive substances for obtaining white solidification are tellurium, bismuth, antimony and materials which evolve hydrogen, such as soluble glass. Their use, however, results in problems because they have a melting point which is lower than that of cast iron or steel, and a boiling point which lies below or within the temperature range of the molten metal on which the measurements are to be taken.

Due to these problems, it has been proposed to use refractory materials as additives in the coating to provide a slight protection of the carbide forming substances, so as to retard the mixing of these substances with the molten metal. The trend has been toward applying these coatings as uniformly as possible on the entire interior surface of the sample cups, probably to achieve a good dispersion of the additives in the metal. The application of these coatings, however, is a time-consuming and costly operation, especially considering the fact that the sample cups may be used only once.

Other problems exist by coating the entire interior surface of the sample cups. Because of the evolution of gases from the coating when the metal is poured into the cup, it has been impossible to fill the cup with metal in one step. Two-step filling of the cup has a detrimental influence on the measurement of the solidifying temperatures. In coating the interior of the cups, the coating was applied after the thermocouples have been placed in them, for economy reasons (otherwise it would have been necessary either to use plugs or to rebore the holes for the thermocouple). This results in an extra coating being applied on the thermocouples. Especially in the case of centrally or axially located thermocouples, when the metal was poured into the cup and gases were evolved from the coating, a slot-like air or gas pocket could be created, resulting in the measurement being inaccurate or even false. In addition, the coating absorbed a certain degree of heat which could effect the accuracy of the measurement.

U.S. Pat. No. 3,546,921, issued to Bourke et al., discloses a method of producing an initial thermal arrest in the cooling curve of a molten sample of hypereutectic cast iron by introducing into the sample a stabilizing additive which retards primary graphite formation as the molten sample cools. The stabilizer is added in the form of a pellet or in particulate form immediately after the sample of molten metal is poured. Alternatively, the stabilizer can be added to the sampling device prior to the introduction of the molten sample. The stabilizing additive includes at least one member of the group consisting of bismuth, boron, cerium, lead, magnesium and tellurium.

The tellurium used in Bourke et al. is not mixed with refractory materials to slow the mixing of the tellurium with the molten metal. As a result, the tellurium pellet tends to become burned up and not available for white solidification. The efficiency of the tellurium in promoting white solidification is greatly dependent on the pouring temperature of the molten metal. If the pouring temperature is too high, a part of the tellurium will burn, resulting in only partial white solidification. If the pouring temperature is too low, the sample will solidify before becoming thoroughly mixed with the tellurium, again resulting in partial white solidification.

Another problem inherent in the use of carbide stabilizers in pellet form or particulate form is the tendency for the stabilizer to rise to the surface of the molten metal as a slag. This is particularly true with higher carbon equivalent irons. When this occurs, the poured iron is not completely chilled so as to obtain a white sample.

In the foundry industry, there is a commercially used mold dressing, purportedly in accordance with U.S. Pat. No. 3,275,460, issued to Jeanneret, which I believe is the closest material to the blob used in this invention.

SUMMARY OF THE INVENTION

The present invention overcomes the problems associated with the prior art processes and apparatus used to promote the white solidification of molten metals.

The problems of the prior art are overcome by attaching a blob of material to the inside of the molten metal cup. The blob includes a carbide formation promoting material mixed with a refractory material and preferably, a material for evolving hydrogen. The refractory material aids in preventing the carbide formation promoting material from being burned up and mixing too quickly with the molten metal. The hydrogen evolving material aids in thoroughly mixing the carbide formation promoting material throughout the molten metal when the molten metal is poured into the cup.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE PREFERRED EMBODIMENTS

Figure 1:
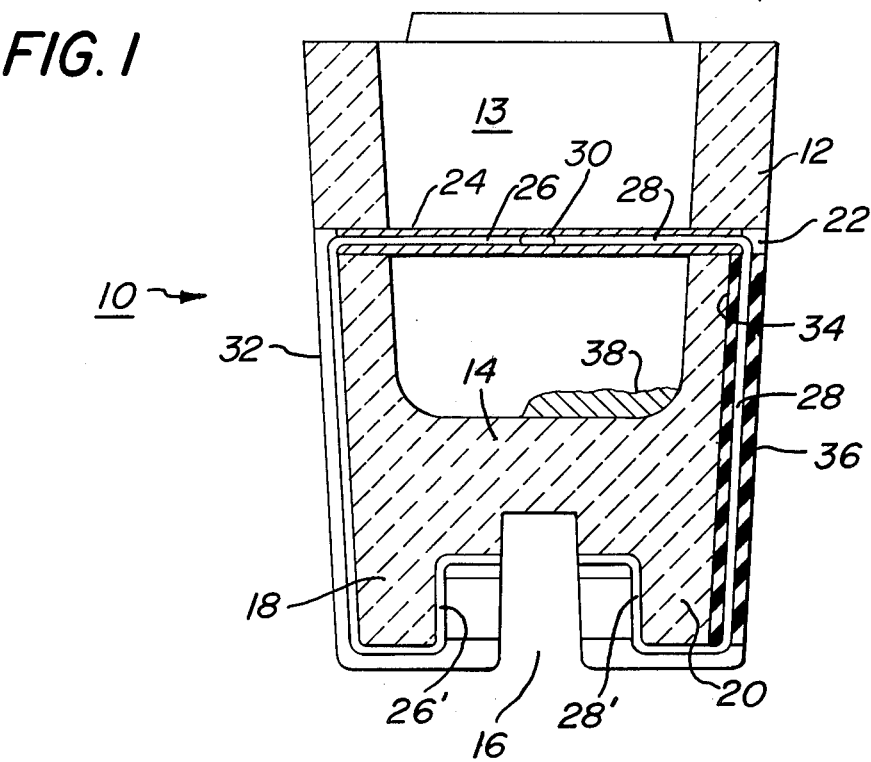
FIG. 1 is a sectional view of a molten metal sample cup having a blob of material attached to its inner surface according to the present invention.

Referring to the drawings in detail, wherein like numerals indicte like elements, there is shown in FIG. 1 a molten metal sample cup designated generally as 10 used in detecting phase changes as a sample of molten metal therein cools.

The phase change device 10 includes a cup 12 made from a conventional refractory material such as foundry sand and refractory cement. The cup 12 has a cavity 13 for receiving a sample of molten metal. The bottom wall 14 of the cup 12 is provided with a recess 16 thereby defining like portions 18 and 20.

A bore 22 extends through oppositely disposed walls of the cup 12. Bore 22 is provided in a location so that its axis will pass through the central axis of cavity 13. A protective shield 24 extends across the cavity 13 and its ends are supported by the bores 22 in the walls of the cup 12. Shield 24 is annular in cross section and transparent to radiation. The preferred material for shield 24 is quartz. Other conventional materials of a similar nature may be utilized.

The thermocouple wires 26 and 28 may be any one of the typical thermocouple materials utilized heretofore in connection with disposable thermocouples such as chromel and alumel which are used with hypereutectic cast iron samples. The juxtaposed ends of the thermocouple wires 26 and 28 are joined together at the hot junction 30 positioned adjacent to the central axis of cavity 13. The hot junction 30 is preferably formed in situ whereby the wires 26 and 28 are inserted into the shield 24 until they are in abutting contact. Slight pressure maintains thermocouple wires in intimate contact while sufficient heat is applied radially inwardly through the shield 24 to effect a welded hot junction 30.

The thusly formed thermocouple assembly is then inserted through the aligned bores 22. The exposed portions of the thermocouple wires 26 and 28 are bent downwardly so as to extend into the vertically disposed grooves 32 and 34 on opposite sides of the cup 12. One of the thermocouple wires, such as wire 28 is provided with an electrical insulating sleeve 36 so as to prevent contact between the thermocouple wire 28 and the material of the body of cup 12. The free end portion of thermocouple wire 26' is bent into the recess 16 to thereby form a contact member for coupling with any mating contacts associated with a recorder. Similarly, the bare free end portion of thermocouple wire 28 is bent into the recess 16 to form a contact portion 28' which is exposed for contact with elements associated with a recorder.

The dimensions of the shield 24 and the thermocouple wires may vary widely. In a typical embodiment of the invention, shield 24 has an OD of 0.069-0.079 inches, and an ID of 0.029-0.039 inches. In connection with such a shield 24, the OD of wires 26 and 28 is 0.025 inches.

The particular embodiment of the cup 12 described above is for illustrative purposes only. Thus, the thermocouple assembly and blob 38 of the present invention may be utilized in any one of a wide variety of different commercially available cups used as phase change detector sample cups.

Figure 2:
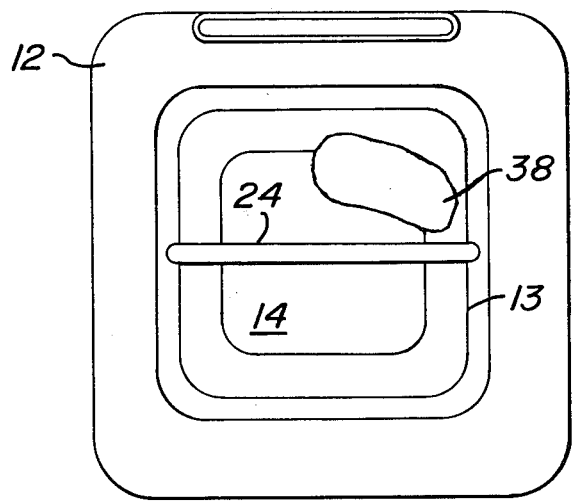
FIG. 2 is a plan view of a molten metal sample cup having a blob of material attached to its inner surface according to the present invention.

Attached to cup 12 within cavity 13 is a blob 38 containing a material for promoting carbide formation. The blob should not coat a substantial portion of the inside of the cup. Preferably, about 1 cubic centimeter of the material forming the blob should be placed in a typical cup whose cavity has a volume of about 50 cubic centimeters (3 cubic inches). The material forming the blob should not be applied as a coating, for the reasons discussed above. Rather, the blob should be a mass of material attached to bottom wall 14 of cup 12 within cavity 13. Preferably, blob 38 will adhere to bottom wall 14 and to two adjacent side walls of the interior of cup 12. This is best shown in FIG. 2.

The blob contains refractory material and a material which promotes carbide formation in the molten metal. Preferably, the blob should also contain a material for evolving hydrogen when the blob is contacted by molten metal. The hydrogen evolving material contained within the blob promotes more thorough and efficient mixing of the carbide formation promoting material in the molten metal. By mixing refractory material with the carbide formation promoting material, the carbide formation promoting material is released from the blob and mixed with the molten metal over a period of time, rather than almost instanteously, as when only the carbide formation promoting material is used alone. This prevents a substantial portion of the carbide formation promoting material from being burned off when the molten metal comes in contact with it.

A preferred refractory material for use in forming the blob is a mixture of about 60 percent silica and about 40 percent alumina. The term "percent" as used in this specification and claims means weight percent and is based on the total weight of the composition under discussion. The refractory material is a conventional, readily available material and may contain small amounts of other metallic oxides, such as ferric oxide, calcium oxide and magnesium oxide. The blob contains refractory material in the amount of about 20% to about 50% of the weight of the blob.

The material for promoting carbide formation and, therefore, white solidification of hypereutectic iron, is a metal selected from the group consisting of bismuth, boron, cerium, lead, magnesium and tellurium. Tellurium is the presently preferred material and should be in crystalline form. The tellurium crystals are preferably 100 mesh in size.

The material for promoting carbide formation is present in the blob from about 10% to about 30% of the total weight of the blob. When tellurium is used, it is present in the preferred range of about 10% to about 30%.

White solidification of molten iron can be improved with hydrogen. Hydrogen not only accelerates nucleation, but also causes a boiling effect, improving the mixing of the carbide formation promoting material in the molten iron. Preferably, hydrogen is evolved from the water of crystallization in water glass which is incorporated in the blob from about 30% to about 60%. The correct amount of water glass or other hydrogen evolving material to be added to the blob may be determined by simple experimentation so that maximum boiling action is achieved without causing the molten metal to overflow from the cup. The presently preferred water glass has a $SiO_2$ to $Na_2O$ ratio of about 3.17 and a density of about 37 to about 40 Baume.

The formation of a refractory blob containing a material for promoting carbide formation and including the preferred hydrogen evolving material in accordance with the present invention will now be illustrated in more detail with reference to the following specific, non-limiting example:

EXAMPLE I 200 g ± 5 of refractory material comprising about 60% silica and about 40% alumina is sieved through a 500 micron sieve. About 190–200 cc (256–269 g) of water glass is placed into a mixing receptacle. While stirring, about 100 g ± 3 of tellurium in crystal form, about 100 mesh in size, is added to the water glass. The tellurium and water glass mixture is stirred for at least 5 minutes. The refractory material is slowly added, while stirring, to the water glass/tellurium mixture and stirred for 10 minutes. The viscosity is then measured. The viscosity should be such that it takes about 9.5 to about 11.5 seconds to fill a graduated glass of 100 cc with a flow cup of 11 mm.

After the mixture has been prepared, about 1 cc ± 0.15 of the mixture is poured into a molten metal sample cup to form a blob within the cavity of the cup. Preferably, the blob of material is poured into one corner of the cup so that it will adhere to the bottom and to two adjacent walls of the cup. The material should not be coated over the bottom of the cup.

The blob is then dried in the cup at an ambient temperature for a minimum of 12 hours, and then placed into an oven at 115° C ± 5° for a minimum of 12 hours to effect a final cure to adhere or bond the blob to the cup within cavity 13.

Cups containing a blob of material prepared in accordance with this example were used to receive a sample of hypereutectic cast iron. A carbon equivalent test resulted in excellent white samples with greater uniformity of results. Since the blob was adhered to the interior of the cup, a layer of slag did not form on the surface of the molten hypereutectic cast iron.

Be referring to Example I, a person of ordinary skill in the art could readily determine the necessary proportions for making blobs of other materials for promoting carbide formation other than tellurium in relation to the refractory material and, if desired, to the hydrogen evolving material.

By using a carbide formation promoting material mixed with a refractory material and a hydrogen evolving material, the carbide formation promoting material will be liberated slowly because of the thickness of the blob and the presence of the refractory material. The mixing of the carbide formation promoting material with the molten metal is efficient due to the hydrogen evolving material present in the blob. Because the cooling of the molten metal in a cup will be much higher with a coating than with a blob, due to the smaller contact surface of the blob, the molten metal sample cups of the present invention may be used at a lower pouring temperature of the molten metal in comparison with standard cups provided with a coating which still guarantees a white solidification. Thus, the cups of the present invention may be used over a wider range of pouring temperatures with excellent results.

The present invention may be embodied in other specific forms without departing from the spirit or essential attributes thereof and, accordingly, reference should be made to the appended claims, rather than to the foregoing specification as indicating the scope of the invention.

I claim:

1. In a device for use in determining phase change of a molten metal comprising a refractory cup having a cavity for receiving molten metal and temperature sensing means supported by said cup, the improvement comprising a blob attached to said cup within said cavity, said blob containing a first material for promoting carbide formation mixed with a refractory material for delaying dispersion of said first material into a sample of molten iron, said blob containing a second material capable of evolving hydrogen when contacted by molten iron, said second material being waterglass, whereby said first material for promoting carbide formation may be thoroughly mixed with said molten iron.

2. A device according to claim 1 wherein said first material is selected from the group consisting of bismuth, boron, cerium, lead, magnesium and tellurium.

3. A device according to claim 2 wherein said first material is tellurium crystals.

4. A device according to claim 3 wherein said tellurium crystals are 100 mesh in size.

5. A device according to claim 2 wherein said blob comprises from about 20 to about 50 percent refractory material, from about 10 to about 30 percent of said first material for promoting carbide formation, and from about 30 to about 60 percent water glass.

6. A device according to claim 5 wherein said blob comprises from about 10 to about 30 percent tellurium crystals.

7. A device according to claim 6 wherein said blob comprises from about 34 to about 37 percent refractory material, said refractory materials comprising about 60 percent silica and about 40 percent alumina, from about 17 to about 19 percent tellurium crystals, and from about 45 to about 48 percent water glass.

8. A device according to claim 6 wherein said water glass has a $SiO_2$ to $Na_2O$ ratio of about 3.17 and a density of about 40 Baume.

9. A device according to claim 1 wherein said blob is bonded to the bottom of said cup within said cavity.

10. A device according to claim 1 wherein said blob is attached to the bottom of said cup and to two adjacent walls within said cavity.

11. A device according to claim 1 wherein said sensing means includes thermocouples of a type for use with molten cast iron.

* * * * *